United States Patent [19]
Daikuzono

[11] Patent Number: 5,415,654
[45] Date of Patent: May 16, 1995

[54] LASER BALLOON CATHETER APPARATUS

[75] Inventor: Norio Daikuzono, Chiba, Japan

[73] Assignee: S.L.T. Japan Co., Ltd., Tokyo, Japan

[21] Appl. No.: 131,666

[22] Filed: Oct. 5, 1993

[51] Int. Cl.⁶ .............................................. A61M 29/02
[52] U.S. Cl. .......................................... 606/15; 606/7; 606/28; 606/194
[58] Field of Search ................... 606/7, 13, 14, 15, 16, 606/192, 193, 194; 604/89; 607/138

[56] References Cited

U.S. PATENT DOCUMENTS

| | | | |
|---|---|---|---|
| 4,878,495 | 11/1989 | Grayzel | 606/193 |
| 5,007,437 | 4/1991 | Sterzer | 607/138 |
| 5,019,075 | 5/1991 | Spears et al. | 606/7 |
| 5,176,698 | 1/1993 | Burns et al. | 606/194 X |
| 5,190,540 | 3/1993 | Lee | 606/27 |
| 5,273,536 | 12/1993 | Savas | 606/194 X |

Primary Examiner—Peter A. Aschenbrenner
Attorney, Agent, or Firm—Lowe, Price, LeBlanc & Becker

[57] ABSTRACT

A laser balloon catheter apparatus emits laser light, received through optical fiber, via a balloon for irradiating tissue. It includes a laser light emitting means, a coolant supply passage located in the balloon, a coolant discharge passage located in the balloon for discharging the coolant, and a coolant circulating means for supplying the coolant to the balloon through the coolant supply passage to inflate the balloon while discharging the coolant through the coolant discharge passage.

10 Claims, 10 Drawing Sheets

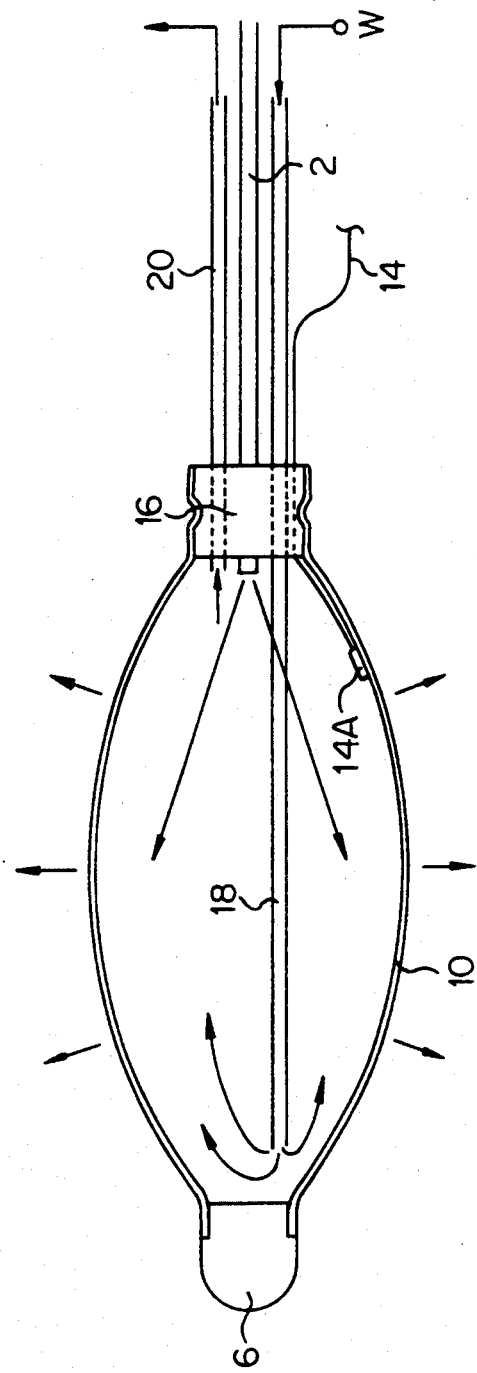

DISTANCE FROM WALLS OF THE URETHRA

LASER BALLOON CATHETER APPARATUS

DETAILED DESCRIPTION OF THE INVENTION

1. Field of the Invention

The present invention relates to a laser balloon catheter which is inserted into the body cavities such as the gullet, the stomach and the prostate for the laser treatment thereof.

2. Prior Art

Laser balloon catheters-are used for opening the clogged portions of the blood vessels. Hyperthermia treatment using the laser balloon catheters for irradiating the cancer tissues with laser lights are conducted.

The structure of such type of the laser balloon catheters is disclosed, for example, in U.S. Pat. No. 4,512,762. In this U.S. Patent, a lumen tube surrounding optical fibers is provided and a balloon is provided at the front end of the optical fibers to surround the front end thereof.

Another structure of the catheter in which a balloon is provided with an acoustic sensor for controlling the vaporization of the tissue is disclosed in U.S. Pat. No. 4,799,479.

However, when a laser balloon catheter is inserted into the urethra to heat the prostate for the treatment thereof, the prostate is located about 5 to 15 mm deeper from the inner wall of the urethra. When the power of the laser lights is increased to heat the prostate to a given temperature, the inner wall of the urethra and the tissue in the vicinity thereof is excessively heated to damage the tissue in the vicinity of the urethra. Curing will become difficult.

Also in treatments other than the prostate treatment, the inner wall of a body cavity into which a laser balloon catheter is inserted is kept at a low temperature to protect the tissue in the vicinity of the inner wall from being thermally damaged and to ensure that tissue which is deeper than the inner wall may to be intensively warmed or heated.

The balloon has been heretofore inflated with air or water and the air. Water has never been circulated through the balloon.

SUMMARY OF THE INVENTION

It is, therefore, an object of the present invention to provide a laser balloon catheter apparatus which is capable of positively penetrating laser light into a deeper position while protecting the tissue in the vicinity of the inner wall where the laser balloon catheter is inserted.

It is another object of the present invention to provide a laser balloon catheter apparatus which is capable of easily controlling the distribution of temperature from the inner wall where the laser balloon catheter is inserted in a depth direction.

It is a further object of the present invention to provide a laser balloon catheter apparatus having coolant circulating means which is capable of stabilizing the inflation of a balloon.

In order to accomplish the above mentioned object, the present invention provides a laser balloon catheter apparatus for emitting in a balloon, laser light which is transmitted through optical fibers and for irradiating the tissue with the laser light transmitted through the balloon, comprising laser light emitting means, a coolant supply passage located in said balloon; a coolant discharge passage for discharging the coolant; and coolant circulating means for supplying the coolant to the balloon through said coolant supply passage to inflate the balloon while discharging the coolant through said coolant discharge passage.

After the laser balloon catheter of the present invention is inserted into, for example, the urethra, the balloon is inflated by supplying coolant, preferably cooling water, thereto. The laser light which have transmitted through the optical fibers is incident from the laser light emitting means upon a target tissue, for example, the prostate. This causes the prostate to be warmed or heated up to the necrotization temperature and will be recovered by metabolic absorption associated with the necrosis.

The distribution of the power of the laser lights in a depth direction of the prostate from the inner wall of the urethra is such that the power of the laser light gradually decreases as the laser light travel in a depth direction from the inner wall. Accordingly, it is necessary to maintain the power of the laser light at a high level in order to warm or heat the deep tissue to a higher temperature.

However, since the power of the laser light incident upon the inner wall of the urethra is higher than the power of the laser light incident upon the central portion of the prostate, the inner wall portion of the urethra is warmed or heated to a higher temperature. As a result of this, the urethra may be thermally damaged.

However, in accordance with the present invention, coolant, for example, cooling water is circulated through the balloon. As a result, the tissue in the vicinity of the inner wall of the urethra is cooled so that the tissue can be protected from being thermally damaged. Since the thermal damage of the tissue in the vicinity of the urethra does not occur, the output of the laser lights can be increased. The deeper tissue in the prostate can be warmed or heated.

If the inner wall portion of the tissue is cooled to, for example, 2° to 15° C., preferably about 3° to 7° C. by circulating the coolant through the balloon of the present invention, pseudo narcotism occurs on the inner wall portion in the tissue. The pain during the operation can be removed or relieved.

In the laser balloon catheter apparatus of the present invention there may be provided temperature detecting means for directly or indirectly detecting the temperature of the tissue which is irradiated with laser light and means for adjusting the emitting rate of the laser lights per unit time in accordance with a signal representing the temperature of the tissue from the temperature detecting means.

The temperature detecting means may have a detecting end which is provided on the surface of the balloon.

The temperature of a target tissue to be irradiated can be positively controlled by adjusting the laser light emitting period of time per unit time based upon the tissue temperature signal from the temperature detecting means.

In accordance with the present invention, there is provided a laser balloon catheter for emitting in a balloon laser light which is transmitted through optical fibers and for irradiating the tissue with the laser light transmitted through the balloon, comprising laser light emitting means; a first guide through which said optical fibers extends and having a front end portion located in the balloon and having at the front end portion a communicating hole which communicates the inside of the guide with the inside of the balloon; securing means for securing the front end portion of the optical fibers to the first guide; a second guide which is provided coaxially with and around the first guide and having a front end which is communicated with the inside of the balloon; and coolant circulating means including a coolant supply passage which is one of a space in said first guide and a space between the first and second guides and a coolant discharge passage which is the other of the spaces, for supplying the coolant through said coolant supply passage to inflate the balloon while discharging the coolant through the coolant discharge passage; a communicating hole for the coolant being formed through said securing means or between securing means and the first guide.

Since application of an excessive force to the optical fibers will break the optical fibers at a higher possibility, it is effective to provide a first guide which surrounds the fibers for protecting the optical fibers and to provide a second guide around the first guide. Coolant can be circulated through a space within the first guide and a space between the first and second guides.

The cooling water circulating means may include a closed cooling water tank, a pressurizing pump to feeding pressurized air to the cooling water tank, a cooling water feeding line having a cooling water circulating pump for pumping to the balloon from said cooling water tank via the cooling water supply passage and a cooling water return line for returning the cooling water in said balloon to the cooling water tank below the water level therein via the cooling water discharge passage. The rate of the circulated cooling water can be controlled by driving said cooling water circulating pump.

Output adjusting means for adjusting the output of the laser lights emitted from the laser light emitting means may be provided. Both of the rate of the circulating water and the output of the emitted laser lights can be controlled by driving said circulated water rate control means and said output adjusting means, respectively in response to the tissue temperature signal from the temperature detecting means.

BRIEF DESCRIPTION OF THE DRAWINGS

FIG. 2 is a schematic view showing an embodiment having a different balloon portion;

FIG. 3 is a schematic view showing another embodiment having different balloon portion;

DESCRIPTION OF THE PREFERRED EMBODIMENTS

Figure 1:
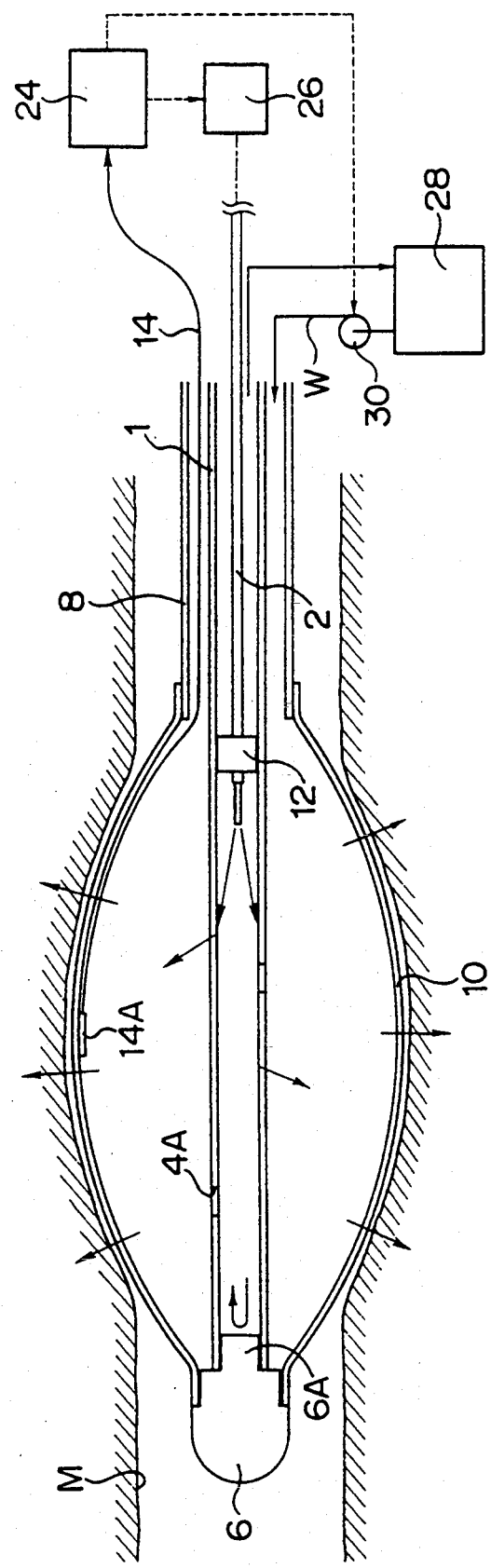
FIG. 1 is a view showing the whole of a laser light irradiation apparatus of the present invention.
Figure 4:
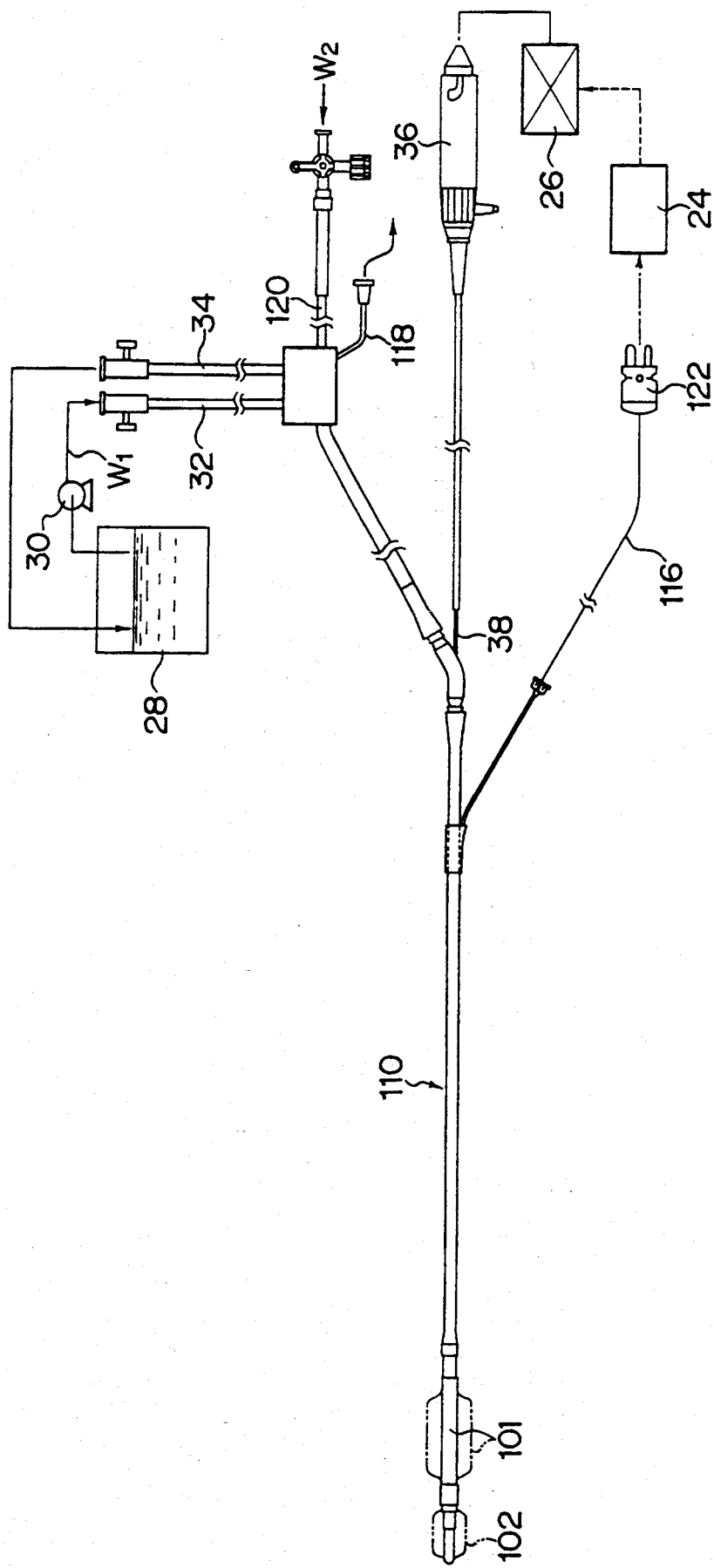
FIG. 4 is a view showing the whole of the laser light irradiation system of the present invention.

The present invention will be more understood by the following description of the preferred embodiments illustrated in the drawings.

FIG. 1 shows the whole of a laser balloon catheter apparatus. An optical fiber represented at 2 is inserted into a first guide 4. The first guide 4 is provided with a shoe member 6 at the front end thereof. A small diameter portion 6A at the rear end of the shoe member 6 is fitted into the first guide 4. The first guide 4 is made of a flexible material such as polyethylene tube through which laser light is transmittable. A second guide 8 which is similarly made of a flexible material such as polyethylene tube is provided coaxially with and around the first guide 4.

A balloon 10 is provided to straddle the front end of the second guide 8 and the shoe member 6 and is secured to the outer surface of the front end portion of the second guide 8 and the outer surface of the shoe member 6 with a bonding agent or code. The balloon 10 is made of an inflatable and laser light transmittable material such as rubber latex.

The optical fiber 2 is secured to a holder 12 in rear of the front end of the first guide 4. The laser light from the laser light generator 26 is transmitted through the optical fiber 2 and emitted from the front end thereof. The laser light emitted from the front end of the optical fiber 2 are transmitted through the first guide 4 and then the balloon 10 and is incident upon a target tissue M. The inner surface of the first guide 4 at least at the front end portion is roughed for scattering the laser light. The rear end face of the small diameter portion 6A of the shoe member 6 and the front face of the holder 12 are coated with a gold plating layer to provide laser light reflecting surfaces so that the laser light is transmitted through the first guide 4 while repeating reflections therebetween.

Coolant, preferably cooling water W is circulated through the balloon 10. Accordingly, the front end portion of the first guide 4 which is located in the balloon 10 is formed with a communicating hole 4A. Part of the holder 12 is also formed with through-hole (not shown). Cooling water W is sucked from a cooling water tank 28 by a circulating pump 30 and is supplied into the balloon 10 through a space between the first and second guides 4 and 8. The cooling water W supplied into the balloon 10 flows into the first guide 4 and through the holder 12 and is then returned to the cooling water tank 28 for recirculation.

A thermocouple 14A is bonded to the inner surface of the balloon 10 and the lead line 14 of the thermocouple 14A is connected to a temperature control unit 24. The temperature of the inner surface of the balloon 10, substantially the temperature of the inner wall of the tissue M is detected and a signal representative of the temperature is input to the temperature control unit 24. The temperature control unit 24 controls the laser light generator 26 to adjust the emitting period of time of the laser lights per unit time and adjusts the circulation rate of the cooling water W circulated by the circulating pump 30 in accordance with the input temperature signal so that the temperature of the inner wall of the tissue M becomes a target temperature.

This enables the temperature of the inner wall of the tissue to become the target temperature and enables the temperature of the warmed or heated tissue to be controlled by controlling the rate of the laser lights incident upon the inner portion of the tissue M. If the temperature of the deep tissue is set as the target temperature, the temperature of the deep tissue can be adjusted to the target temperature by preliminarily determining the temperature of the inner wall of the tissue M and the temperature of the deep tissue and monitoring the temperature of the inner wall of the tissue M.

FIG. 2 shows an embodiment in which coaxial guide means is not provided. An optical fiber is secured to a holder 16 with the front end of the fiber 2 being located within the balloon 10. A cooling water supply tube line 18 and a cooling water discharge tube line 20 are disposed in a parallel relationship with each other to extend through the holder 16. The balloon 10 is provided straddling the holder 16 and the shoe member 6. Cooling water W flowing through the cooling water supply tube line 18 is supplied into the balloon 10 and thereafter discharged through the cooling water discharge tube 20.

It is difficult to insert the catheter forcibly into the tissue since the catheter has no guide means of FIG. 2. This catheter is effective to insert the tube in combination with an endoscope.

FIG. 3 shows another embodiment in which a balloon portion 24A of a second guide 24 surrounding the first guide 22 is secured to the front end of the first guide 22. The second guide 24 can be formed into the balloon portion 24A by blowing a plastic tube made of ethylene vinyl acetate resin which is heated at the front end thereof to enlarge the diameter. Even if cooling water W, the balloon portion 24A is inflated as represented by a phantom line in the drawing. This will not obstruct the insertion of the catheter into the tissue since it reduces the diameter while it deforms.

The balloon portion 24A is inflated and pressed upon the inner wall of the tissue as represented by a solid line in the drawing by supplying the cooling water W into the balloon portion 24A through a space in the first guide 22, the through hole 12A of the holder 12 and the communicating hole 22A.

The laser balloon catheter and the cooling water circulating means of the present invention can be embodied as shown in FIGS. 4 to 7.

First and second balloons 101 and 102 are provided at the front end of tan insertion guide 110. An insertion guide 110 has an inner first guide 112 and a second guide 114 which surrounds the first guide 112. A lead line 116 for a temperature sensor, a urination tube 118 and a second balloon inflating coolant supply line 120 are provided between first and second guides 112 and 114. The lead line 116 for the temperature sensor is connected to a connector 122. A signal representative of the temperature is input to a temperature control unit 24 via the connector 122 for driving a laser light generator 26. Urine is discharged via the urination tube 118 when urination occurs during treatment. For example, water W2 is supplied to the second balloon inflating coolant supply tube line 120.

After fluid for inflating the first balloon 101, for example, water W1 is supplied to a tube 32 from a cooling water tank 28 by means of a circulating pump 30, it flows through a space between the first and second guides 112 and 114 and is used for inflating the first balloon 101 and thereafter flows into the first guide 112 and is returned to the cooling water tank 28. The water in the cooling water tank 28 is adjusted to a given temperature.

Laser light, preferably Nd-YAG laser light, from the laser light generator 26 is transmitted through the connector 36 and the optical fiber 38.

Figure 5:
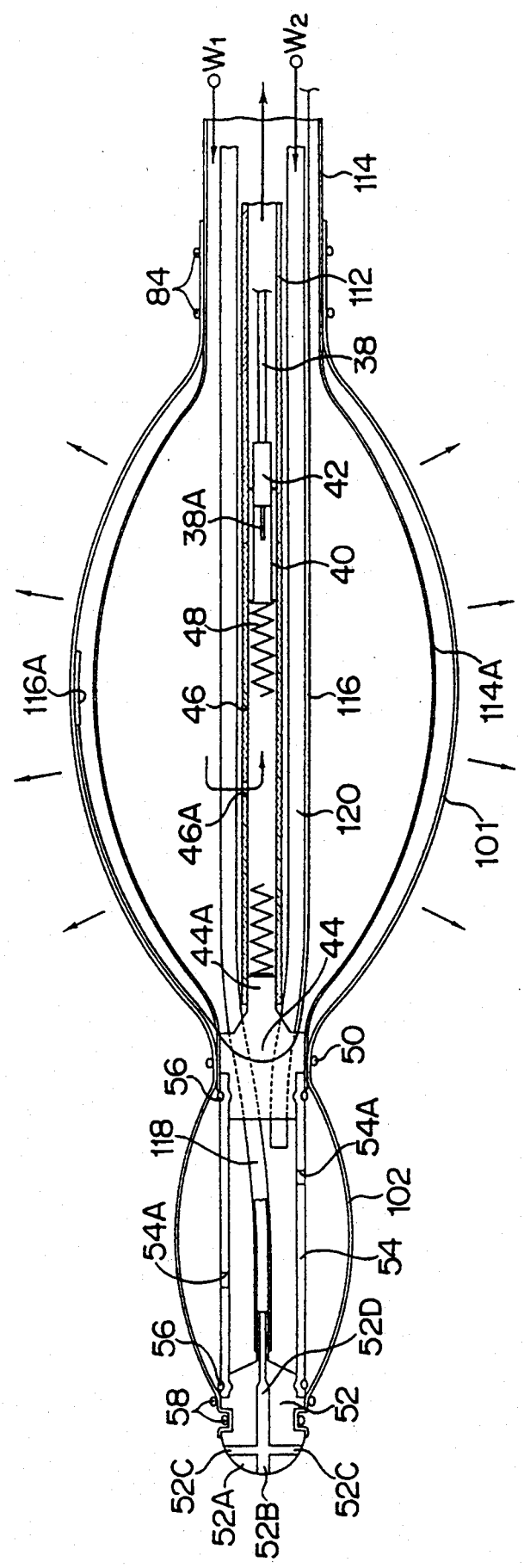
FIG. 5 is a longitudinal sectional view showing the structure of the front end portion of a laser balloon catheter.

The structure of the front end portion of the laser balloon catheter is illustrated in FIG. 5. That is, the optical fiber 38 is provided within the first guide 112 comprising a plastic tube made of polyethylene and the like. A heat resistive protection tube 40 having a high rigidity is provided within the front end portion of the first guide 112. A holder 42 made of metal is disposed within the protection tube 40 for holding the front end of the optical fiber 38.

Figure 6:
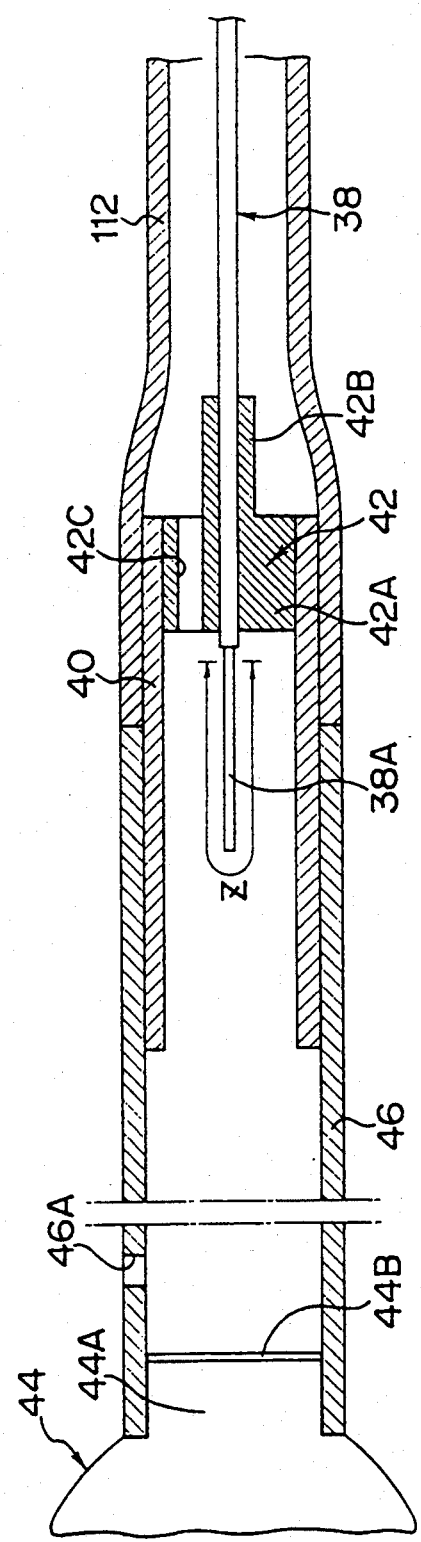
FIG. 6 is an enlarged longitudinal sectional view showing the main part of the front end portion of the catheter.
Figure 7:
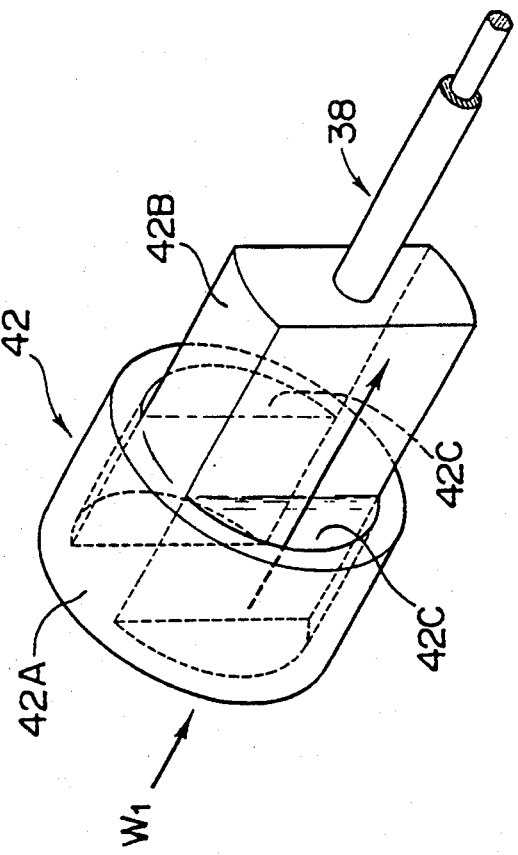
FIG. 7 is a schematic view of a holder.

The manner of holding the optical fiber 38 is illustrated in FIGS. 6 and 7. That is, the holder 42 has a circular portion 42A on the front end side and a flat holding portion 42B on the rear end side. The circular portion 42 is formed with throughholes 42C on both sides thereof. The holder 42 is plated with reflective metal, such as gold for reflecting laser lights. The optical fiber 38 passes through the holding portion 42B and the circular portion 42A. The optical fiber 38 extending beyond the front end of the circular portion 42A has no clad so that a core 38A of the fiber 38 is exposed. Accordingly, laser lights are emitted from the core portion 38A. The laser light is emitted from the front end of the core 38 at a higher percentage in this case. In order to emit the laser lights from the sides of the core at a higher rate, working to provide the core with rough surface, coating of a film including a light scattering material or coating of a film including light absorbing powders such as carbon for converting optical energy into the thermal energy is conducted over the area Z in FIG. 6.

A connector 44 is provided at the laser emitting end which is a front portion extending beyond the front end of the optical fiber. The connector 44 has a diameter reduced portion 44A at the rear end thereof. A first linking tube 46 made of plastics through which laser lights are transmittable is provided straddling the periphery of the diameter reduced portion 44A and the protection tube 40. The first linking tube 46 is disposed on the outer surface of the protection tube 40 in such a manner that it abuts upon the front end of the first guide 112. The first linking tube 46 is formed with a communicating hole 46A on an appropriate position. A coil spring 48 is provided within the first linking tube 46 between the rear end of the diameter reduced portion 44A and the front end of the protection tube 40. The coil spring 48 is plated with a laser light reflective film such as gold on the outer surface thereof. The diameter reduced portion 44A is coated with a laser light reflective film, such as gold coating layer 44B on the rear end surface thereof. In a preferred embodiment of the present invention, the laser lights are scattered on the inner surfaces of the first linking tube 46 and the protection tube 40. An approach to scatter the laser light may include working of the inner surfaces of the first linking tube 48 and the protection tube 40 into rough surfaces and depositing powders of alumina or silica on the inner surface by baking.

The second guide 114 is formed of a flexible plastic material such as ethylene vinyl acetate or polyethylene and has a preliminarily inflated portion 14A at the front end thereof. The front end portion of the second guide 114 surrounds the periphery of the connector 44 and is secured 114 together with the first balloon 101 by being bound with fastening means such as a code 50.

On the other hand, a shoe 52 made of, for example, a metal is provided in front of the connector 44. The shoe 52 is linked with the connector 44 by a second linking tube 54 made of a flexible plastic which constitutes second linking means. The second linking tube 54 is secured at the opposite ends thereof to the shoe 52 and the connector 44 by being bound with codes 58. The linking tube 54 is formed with a through-hole 54A.

In the embodiment, a tube which constitutes the first balloon 101 extends forward to the shoe 25 through the connector 44 to provide the second balloon 102. In another embodiment of the present invention, the first balloon 1 may be separated from the second balloon 102. The front end portion of the second balloon 102 is secured to the shoe 52 by being bound with fastening means such as code 58. The first and second balloons 101 and 102 are made of an expandable material having a flexibility and an elasticity. They are made of rubber latex in the embodiment and may be made of silicone rubber.

The shoe 52 includes a semi-spherical portion 52A at the front end thereof, a cylindrical portion at the intermediate position and a small diameter portion at the rear end thereof. The semi-spherical portion 52A is formed with main urination opening 52B and subsidiary urination openings 52C which open at the center and both sides of the portion 52A and are communicated with a common urination tube 52D which opens at the rear end of the small diameter portion.

The urination tube 118 which is fitted into the small diameter portion of the shoe 52 extends through the connector 44 and passes through the first guide 114 and opens externally as shown in FIG. 1. Accordingly, when urination occurs during an surgical operation, urine flows into any of the urination openings and is externally discharged via the urination tubes 52D and 18. Such urination means provides a very effective means since heating of the prostate promotes urination in a prostate operation. The reason why the urination openings are provided at the center and on both sides of the semi-spherical portion 52A is to smoothly discharge urine via the openings if any of the openings is clogged with the bladder.

On the other hand, the second balloon inflating coolant supply tube line 120 extends into the first guide 14 and extends through the connector 44 and enters the second linking tube 54. The cooling water W2 which is externally supplied flows through the second balloon inflating coolant supply tube line 20 and supplied into the second linking tube 54 and then introduced into the second balloon 102 via the communicating hole 54A for inflating the second balloon 102. The second balloon 102 is deflated by draining the cooling water W2 via the second balloon inflating coolant supply tube line 20.

As shown in FIG. 5, the lead line 116 of the temperature sensor extends through a space between the first and second guides 12 and 14 and around the outer periphery of the connector 44 and then extends through the second guide 114 and is in contact with the inner surface of the first balloon 102 in the intermediate position along the length thereof. The front end of the lead line 116 is sandwiched between reflecting strips made of two aluminum foils and plastic sheets containing white pigment for reflecting light. The reflecting strips 116A are bonded to the inner surface of the first balloon 101 with a boding agent.

The laser balloon catheter may be preferably used for the treatment of the prostate. When the cooling water W1 and W2 is not pumped at a pressure, the first and second balloons 101 and 102 are deflated by their own deflating power. At this time, the inflatable portion 114A of the second guide 114 is also deflated in association with the deflation of the first balloon 101.

Figure 8:
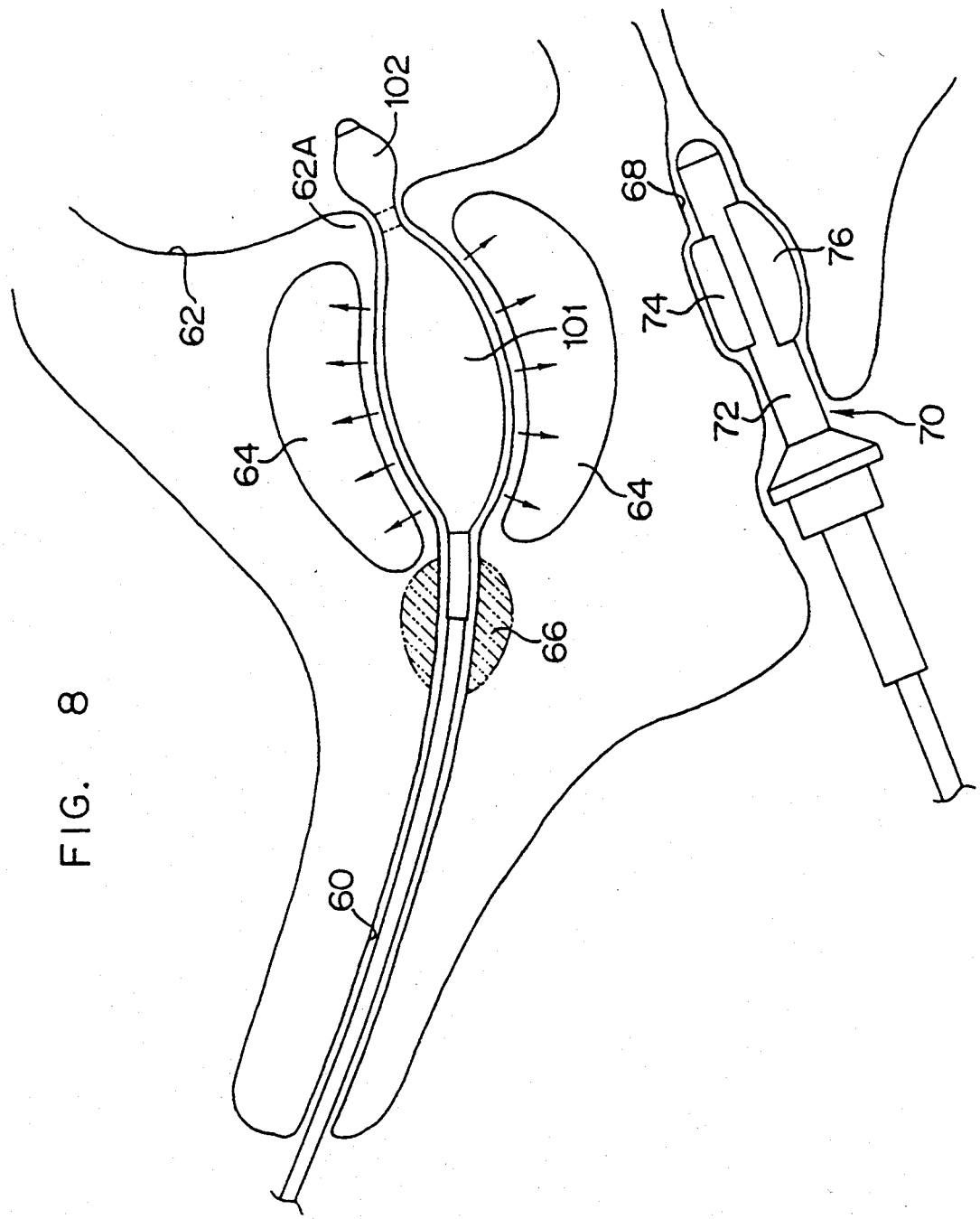
FIG. 8 is an explanatory view showing the treatment of the prostate.

In this condition, the laser balloon catheter is inserted into the urethra 60 to position the second balloon 102 in the bladder 62 as shown in FIG. 8. Then, the cooling water W1 is supplied to the inflatable portion 114A of the second guide 114 from the cooling water tank 28 by the circulating pump 30 via the tube 32 and a space between the first and second guides 112 and 114 for inflating the inflatable portion 114A. This inflation causes the first balloon 101 to be also inflated as shown in FIGS. 5 and 8. The cooling water W1 used for inflation flows into the first guide 112 via the discharge tube 34 and is returned to the cooling water tank 28 via the communicating hole 46.

The cooling water W2 is also supplied to the second balloon 102 via the second balloon inflating coolant supply tube line 120, the second linking tube 54 and then the communicating hole 54A for inflating the second balloon 102 as shown in FIGS. 5 and 8.

Laser light from the laser light generator 26 is incident upon the optical fiber 38 via the connector 36 and is emitted from the core 38A at the front end of the optical fiber 38. The laser lights incident upon the protection tube 40 or the first liking tube 46 of the emitted laser light is transmitted directly through the tubes 40 and 46 or transmitted therethrough after repeating reflection and diffusion is are ultimately diffused in a lateral direction and is incident upon the prostate 64 via the second guide 114 and the first balloon 101. If some of the forward travelling laser light is incident upon the gold plated coil spring 48 while travelling in a forward direction, they is reflected by the coil spring 48 and is diffused in a lateral direction and is incident upon the prostate 64 via the first linking tube 46, the second guide 14 and the first balloon 101.

The laser light which travel forwardly without colliding with the coil spring 48 is reflected on the gold plated layer 44B and some of them is reflected in a lateral direction while it travel rearward or, collides with the coil spring 48. The reflected light travelling rearward is reflected from the gold plated front surface of the circular portion 42A of the holder 42 and will then travel forward. In such a manner, the laser light is diffused in a lateral direction after repeating the reflections. Therefore, the laser light is emitted toward the prostate from the entire surface of the first balloon 101 at a higher amount of light in the central position along the length of the balloon and at a lower amount of light at the opposite ends of the balloon 101.

The laser light which is incident upon the prostate 64 is absorbed by the tissue in the prostate 64 to generate heat. As a result., the prostate 64 is warmed or heated.

Heating with the laser lights are maintained for a given period of time. The diseased tissue in the prostate 64 is thus heated on exposure to laser light to necroses and the other tissue of the prostate will recover soon after operation.

Heating of the prostate with ultrasonic waves is possible. Although many of the ultrasonic waves are absorbed by the water content in the tissue of the prostate, the ratio of the laser lights absorbed by the tissue is lower and the curing effect is low. In contrast to this, the ratio of the laser light, in particular, Nd-YAG laser light absorbed by the water content is about 10% and the rest of the laser light is absorbed by the protein in the tissue. Even if the cooling water is caused to flow through the balloon, most of the laser light is transmitted through the cooling water.

In the embodiment of the present invention, the inside of the first balloon 101 is cooled by the cooling water W1 forcedly circulated through the second guide 114 to keep it at a given temperature. When the forced cooling is not conducted, the power of the laser lights decreases as they travel from the inner wall of the urethra to the deeper portion of the prostate. The inner wall of the urethra is heated to a higher temperature while the deeper portion of the prostate is heated to the lower temperature as represented by the temperature distribution curve in FIG. 9.

If the power of the laser light is increased to heat the tissue from the inner wall of the urethra to the center of the prostate which is about 6 to 12 mm deep therefrom, the inner wall of the urethra and the tissue in the vicinity thereof is excessively heated and may be damaged. It becomes more difficult to cure the damaged tissue.

Figure 9:
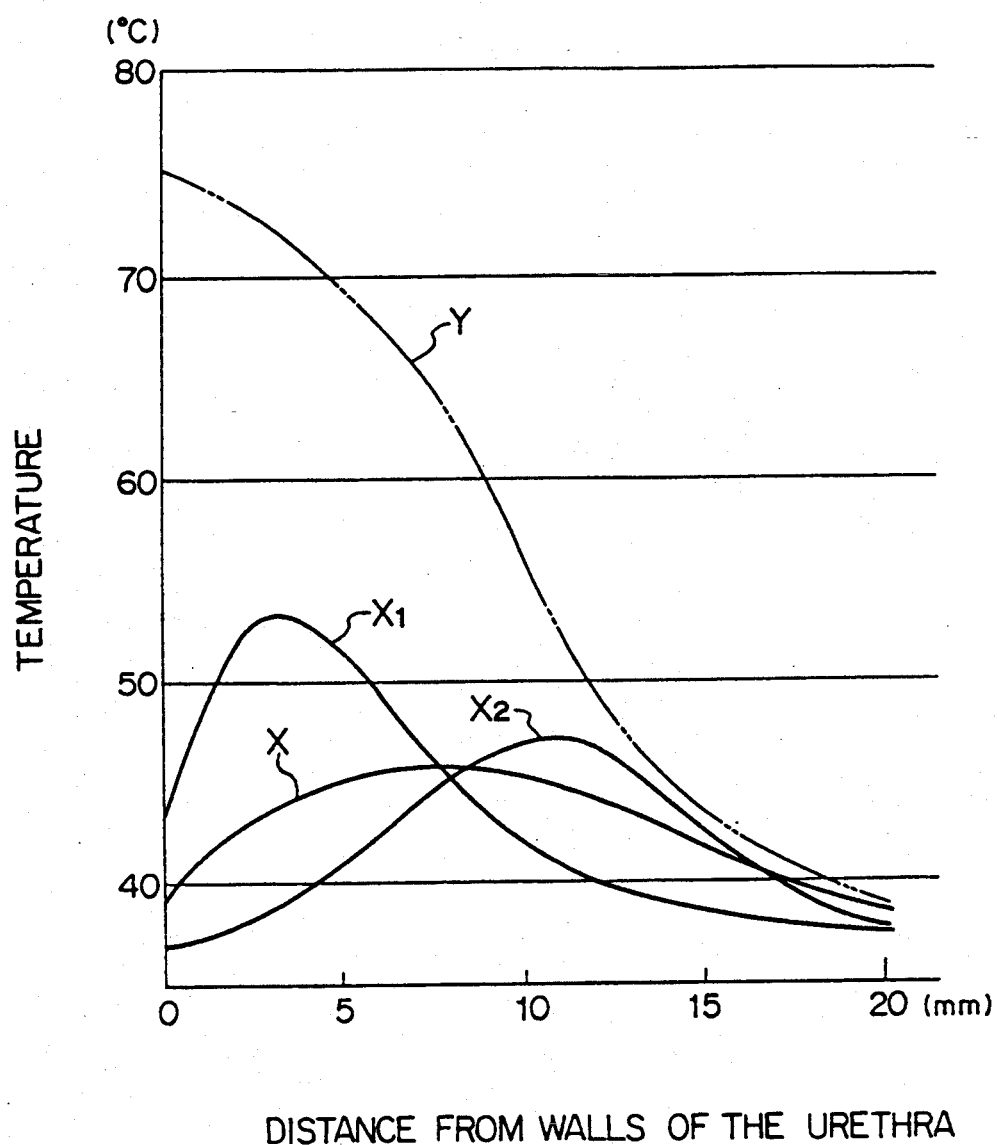
FIG. 9 is a graph showing the distribution of the temperature from the inner wall of the urethra in a depth direction when forced cooling is conducted and not conducted.

When the inside of first balloon 101 and the inflatable portion 114A of the second guide 114 is cooled with the cooling water W1, the tissue in the vicinity of the urethra is cooled as represented by the temperature distribution curve X in FIG. 9 to prevent it from damaging while the laser light is incident upon the central portion of the prostate at an enough amount so that the tissue to the central portion is positively heated. In this case, the temperature distribution can be adjusted as represented by the temperature distribution curve X1 or X2 in FIG. 9 by controlling the power of the laser light and the circulating amount or the temperature of the cooling water W1. Curing effect can be enhanced by adjusting the temperature distribution depending upon the symptoms of the prostate.

For the prostatitis, the inside of the prostate is heated at a temperature not high than 43° C. by forcedly cooling it with the cooling water W1. For the prostatomegaly, the inside of the prostate is heated to 45° C. or higher for necrotization while the inner wall of the urethra and the tissue in the vicinity thereof is protected from the thermal damage by forcedly cooling it with the cooling water W1. The necrosed tissue is metabolically absorbed to reduce the size of the prostate to open the urethra.

The lengths of the balloon 101 and the inflatable portion 114A of the second guide 114 or the position of the front end of the optical fiber 38 is preset in such a manner that the laser lights are prevented from impinging upon the sphincter muscle 66. The balloon having a length of about 2 to 4 cm is effective for the treatment of the prostate.

The second balloon 102 is effective primarily to position the laser balloon catheter and secondarily to prevent the laser balloon catheter from removing from the bladder 62 during operation. That is, the first balloon 101 is positioned in a position corresponding to the prostate by inflating the second balloon 102 and then removing the laser catheter until the second balloon 102 abuts upon the neck portion 62A of the bladder 62 after the laser balloon catheter has been inserted to locate the second balloon 102 in the bladder 62. After completion of this positioning, the first balloon 101 is inflated. Even if the laser balloon catheter is shifted during operation, the laser balloon catheter can be prevented from removing from the bladder 62 since the second balloon 102 would abut on the neck portion 62A of the bladder 62.

The temperature of the inner wall of the urethra is detected by a thermocouple which is provided at the front end of the lead line 116. A signal representing the temperature is input to a temperature control unit 24 via the lead line 116 and the connector 122. The temperature of the inner wall of the urethra is controlled by adjusting the interval of the turn on or off time of the laser light generator 26 depending upon the difference between the detected temperature and a target temperature of the inner wall of the urethra. Control of the temperature of the center of the prostate is possible by preliminarily determining the correlation between the temperature of the center of the prostate and the temperature of the inner wall of the urethra.

Since excessive penetration of the laser light into the prostate to heat it will cause the tissue of the prostate to be damaged, it is preferable to insert a temperature detecting probe 70 into the rectum 68 as shown in FIG. 8. The temperature detecting probe 70 comprises a temperature sensor 74 having a plurality of, for example, 5 thermocouples disposed at the front end of a metal tube having a high rigidity on one side thereof so that the front ends of the thermocouples face externally and a balloon 76 on the other side for biasing the sensor 74. The lead lines for respective thermocouples of the temperature sensor 74 are electrically connected to an external device such as the temperature control unit 24. The biasing balloon 76 is inflated by an external pressure source such as air source after the temperature detecting probe 70 has been inserted into the rectum 68. The inflated balloon 76 will bias the temperature detecting probe toward the rectum 68 and to closely contact with the inner wall of the rectum 68.

Irradiation of the prostate 64 with laser light causes the prostate to be warmed or heated. Some of the laser light is transmitted through the prostate 64 to reach the side of the rectum 68 so that the tissue in the vicinity of the rectum 68 is also heated. If the temperature of the inner wall of the rectum 68 which is detected by the temperature sensor 74 exceeds a preset temperature, the turn-off period of time of the laser light generator 26 is extended or the power of the laser lights is lowered to prevent excessive heating of the prostate Thermal damage on the rectum 68 can be also prevented.

Figure 10:
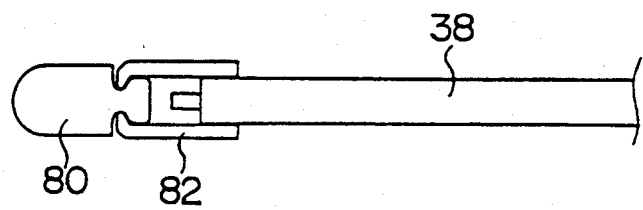
FIG. 10 is a longitudinal sectional view showing an embodiment in which a chip is used as a laser emitting end.

The present invention includes a further embodiment which is illustrated in FIG. 10. The optical fiber is not provided as means for emitting laser light. A chip 80 through which the laser lights are transmitted is provided in front of the optical fibers 38. The laser light from the front end of the optical fibers 38 is incident upon the chip 80 so that the laser light are ultimately emitted from the chip 80. The optical fibers is linked with the chip by an appropriate linking fitting In a further embodiment, the inflating portion 114A of the second guide 14 does not extend to the connector 44 through the first balloon i and is terminated slightly in front of a code for fastening the first balloon 101 of FIG. 5 to the second guide 14 so that the first balloon 101 is inflated directly by pumping the cooling water W1.

A double film structure of the first balloon 101 and the second guide 14 in which the inflatable portion 114A of the second guide 14 extends to the connector through the first balloon 1 provides various advantages. If the first balloon 101 is made of rubber latex, the inflated first balloon 101 will become semispherical in shape, and is difficult to become elliptical in longitudinal section. Accordingly, a plastic tube is preliminarily provided and the plastic tube is pressurized and heated at the front end portion thereof for blow working to form the inflating portion 114A having the same and large diameter. When the inflating portion 114A is inflated, it will not be inflated beyond the preliminarily fabricated shape. As a result, the shape of the inflated first balloon 101 will follow the shape of the inflatable portion 114A. A second advantage is that the front end of the lead line 116 is adhered to the inner surface of the first balloon 101 by the introduction of the lead line 116 between the first balloon 101 and the inflated portion 114A to prevent an error in detected temperature from occurring when the inflating portion 114A is inflated even if the front end of the lead line 114 should be separated from the inner surface of the first balloon. A third advantage is that leakage of water is prevented by the double film structure even if one of the films is torn. The inflatable portion 114A of the second guide 114 is automatically deflated by the deflating power of the first balloon 101 if the cooling water introduced to the inflatable portion 114A is drained.

Although the cooling water W1 flows through a space between the first and second guides 112 and 114 and flows into the first guide 112 through the communicating hole 46 and is discharged through a space in the first guide 112 in the above mentioned embodiment, the direction of the flow of the cooling water may be reversed.

The reason why the first linking tube 46 is provided separately from the first guide 112 is to make easier the assembling such as setting of the holder 42 and the protection tube 40 on the front end portion of the first guide 12 and setting of the spring 48 within the first linking tube 48. Accordingly, the first linking tube 46 may be omitted and the first guide 112 may extend to fit into the small diameter portion 44A. In this case, the first guide 112 is formed with a communication hole for the cooling water W1.

Although Nd-YAG laser light is most preferable as the laser light mentioned above, argon laser light or diode laser lights and the like may be used. Since the laser light is absorbed by water at a very low percentage, it transmitted through the cooling water and is impinged upon the tissue at an enough rate.

Although cooling water is used for inflating the first and second balloons 1 and 2, air, nitrogen gas and carbon oxide gas and the like may be used. Other cooling liquid such as alcohol may be used.

In order to smoothly insert the laser balloon catheter of the present invention into the tissue, it is preferable that the first and second guides 112 and 114 and the first and second linking tubes 116 and 54 be flexible. If it suffices to insert the catheter rectlinearly, at least one of these components may be non-flexible.

Figure 11:
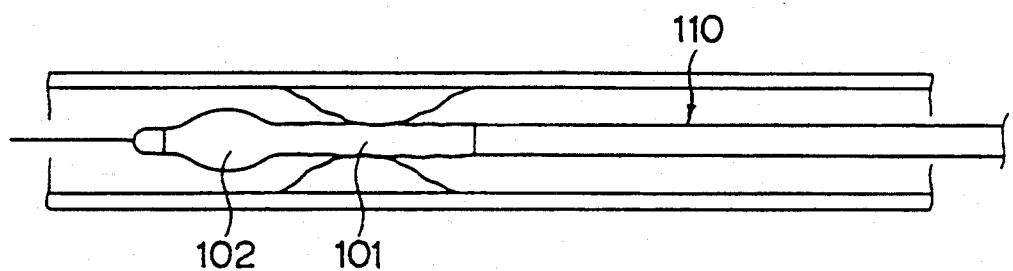
FIG. 11 is a schematic view showing the manner in which the laser balloon catheter is inserted into the stricture of the blood vessel.
Figure 12:
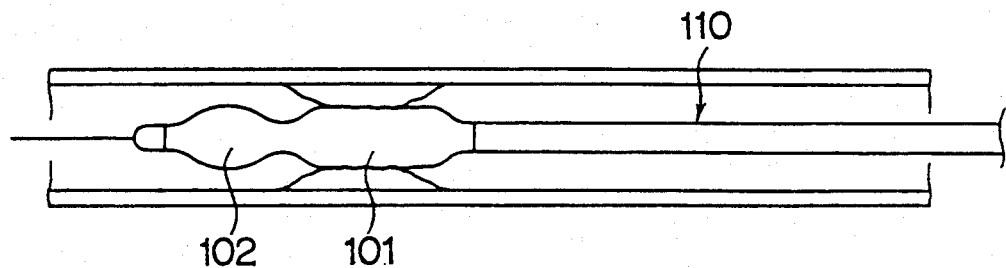
FIG. 12 is a schematic view showing the manner in which the stricture of the blood vessel is irradiated with the laser lights.

The laser balloon catheter of the present invention is also effective for the treatment of the other tissues. For example, the catheter is effective for expanding a stricture N of the blood vessel V as shown in FIG. 11. In this ease, a guide wire 84 is preliminarily inserted into the urination tube 118. After or while the guide wire 84 is inserted into the target blood vessel V, the laser balloon catheter is inserted into the vessel V. Subsequently, the second balloon 102 is inflated as shown in FIG. 11. Thereafter, the laser balloon catheter is removed. When the shoulder at the rear end of the second balloon 102 abuts on the stricture N, a surgical operator recognizes the presence of the stricture N in rear of the second balloon 102 by the hand's feeling. While the first balloon 101 is inflated in this position, the stricture N is irradiated with the laser lights to be vaporized for expanding the vessel as shown in FIG. 12.

Figure 13:
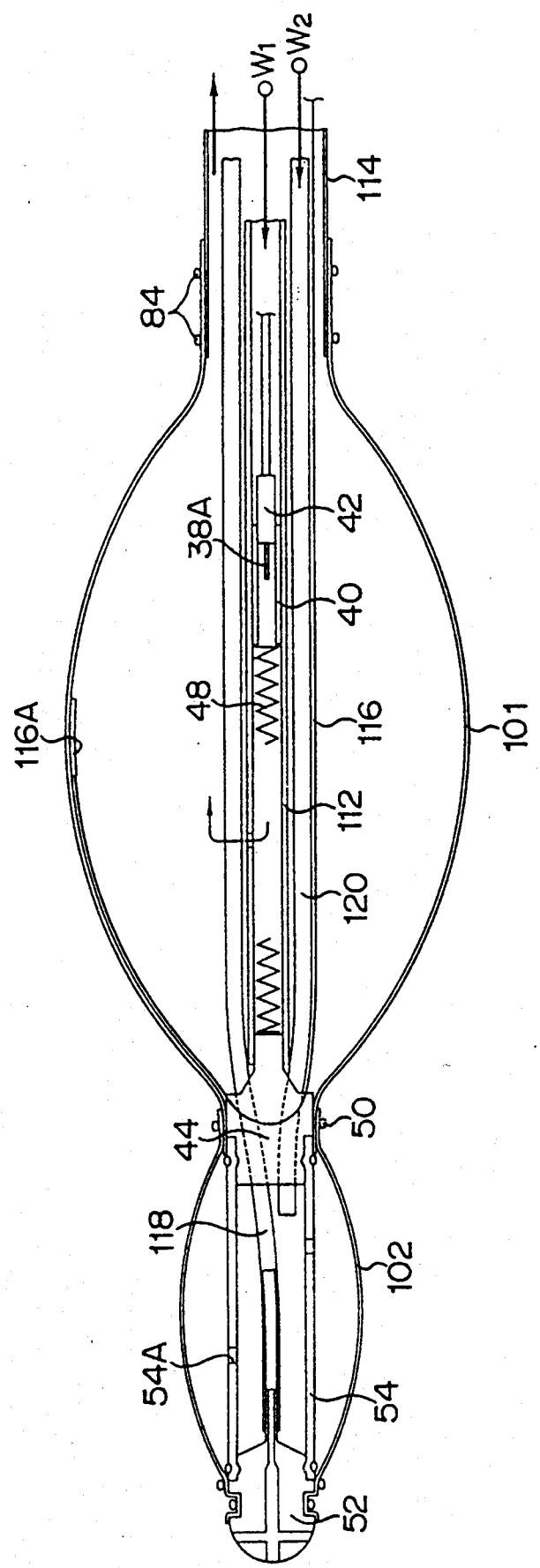
FIG. 13 is a longitudinal sectional view showing the structure of an another laser balloon catheter.

FIG. 13 shows a further embodiment in which the first balloon 101 is provided separately from the second balloon 102, the second guide 114 does not extend forward, the first balloon 101 is not a double film structure but a single structure and the first guide 112 extends to fit into the small diameter portion 44A. In this embodiment, the first guide 112 constitutes the first liking means.

Figure 14:
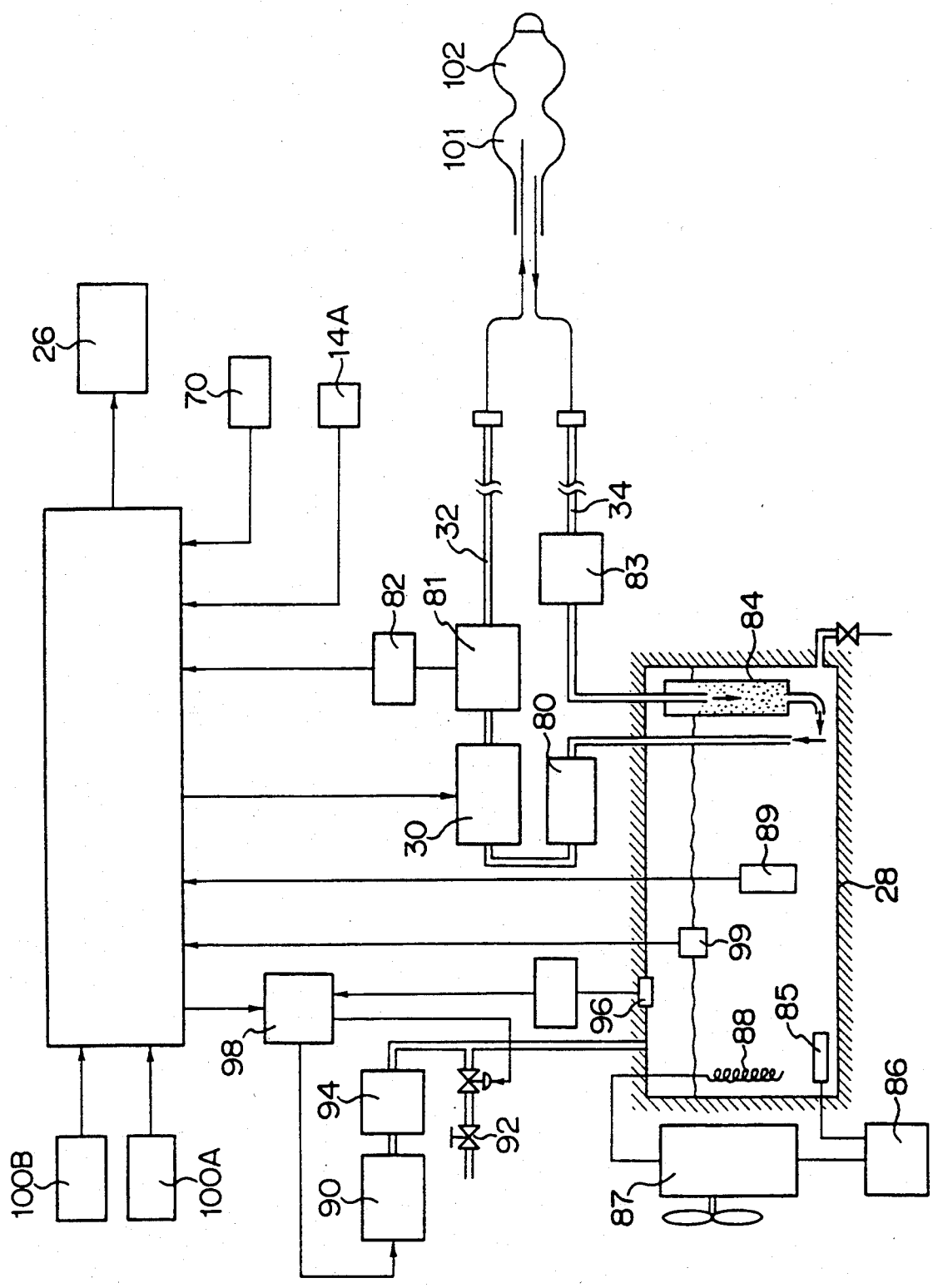
FIG. 14 is a schematic view showing a cooling water circulating line.

In the present invention, the flow rate of the cooling water is preferably controlled based upon the signal representing the temperature the tissue. At this end, the structure shown in, for example, FIG. 14 is adopted. The cooling water circulating pump 30 is driven by the temperature control unit 24 in response to a signal from the temperature detecting end 14A such as thermocouple for controlling the circulating rate of the cooling water in the balloon 101. Simultaneously, the laser light generator 26 is driven to control emitting rate of the laser lights per unit time.

The cooling water is pumped into the tube 32 through the filter 80 from cooling water tank 28 which is adiabatically insulated by an adiabatic material. A flow rate meter 81 is provided in the tube 32 in the length thereof for detecting the current flow rate via an amplifier 82. The control rate of the cooling water circulating pump 30 is determined based upon the deviation between the current flow rate and the target flow rate. A reference numeral 83 denotes a flow rate meter which is provided in the discharge tube 34 in the length thereof. A water purifying column 84 which is filled with ion exchange resin is provided at the exit of the discharge tube 34.

A chiller unit 87 is driven by a chiller controller 86 based upon a signal representing the temperature of water from a water temperature detector 85 so that the cooling water in the cooling water tank 28 is controlled to a given target temperature by a cooling coil 88. In order to determine the circulation rate of the cooling water circulated by the cooling water circulating pump 30, the temperature of the cooling water in the cooling water tank 28 is detected by the water temperature sensor 89 and is input to the temperature control unit 24.

It is possible to inflate the balloon 101 by providing the difference between the rates of the cooling water supplied to the balloon 101 and discharged therefrom. Since there is a change in the rate of the cooling water, the inflation rate of the balloon 101 is unstable. Accordingly, it is better to inflate the balloon 101 by applying pressurized air to the cooling water tank 28 which is converted into a closed tank. At this end, an air pump 90 is communicated with the cooling water tank 28 via a pressurized air tube 91. The pressure of the air pumped by the air pump is controlled depending upon the inflation of the target balloon 101. Reference numerals 94 and 95 denote a mist filter and a safety valve, respectively.

Since application of an excessive pressure may break the balloon 101, the opening of the leak valve 92 is preliminarily coarsely adjusted and the opening of the electromagnetic valve 93 is finely adjusted to control the inflation degree of the balloon 101 in response to a signal of the pressure in the cooling water tank 28 from the pressure gauge 96. A reference numeral denotes a water amount detector.

There is a risk that the tissue is thermally damaged if the temperature of the cooling water detected by a water temperature sensor 89 becomes excessively high in the event of a failure of the chiller unit 87 and the like. There is a risk that the balloon 101 will be broken if the pressure in the cooing water tank 28 becomes excessively high in the event of a failure of the pressure gauge 96. Accordingly, an interlocking means for stopping the operation of all of the laser light generator 26, the cooling water circulating tank 30 and the air pump 90 is incorporated in the temperature control unit 2.4. Although not illustrated, a pressure gauge 100A is provided in a cooling water supply line leading to the second balloon 102 to prevent the second balloon 102 from being broken due to excessive inflation. A pressure gauge 100B is provided in the urination line to prevent the difficulty of urination due to clogging of the urination line. The interlocking means is operated to stop the operation of all the laser light generator 26, the cooling water circulating pump 30 and the air pump 90 also when the pressures from the pressure gauges 100A and 100B become excessively high. The operation of the laser light generator 26 is stopped or the output thereof is lowered when the temperature of the inner wall of the rectum from the temperature detecting probe 70 become excessively high.

As mentioned above, the laser lights can be positively penetrated into the tissue at a deep position while preventing the thermal damage of tissue in the vicinity of a position where the laser balloon catheter is inserted in accordance with the present invention.

The present invention provides an advantage in that the distribution of the temperature from the inner wall on a position where the laser balloon catheter is inserted in a depth direction can be easily controlled.

The laser balloon catheter apparatus of the present invention is effective for the treatments of the tissues of the gullet, the stomach, the duodenum, the blood vessel as well as the treatment of the prostate. The catheter is also applicable to the hyperthermia treatment for the cancer tissue.

What is claimed is:

1. A laser balloon catheter apparatus emitting laser light received through optical fiber via a balloon for irradiating tissue, comprising:
   laser light emitting means comprising holder means holding a distal end portion of an optical fiber so as to enable emission of laser light from an end face of the optical fiber;
   a coolant supply passage located in said balloon for supplying a coolant thereto;
   a coolant discharge passage located in said balloon for discharging the coolant; and
   coolant circulating means for supplying the coolant to the balloon through said coolant supply passage to inflate the balloon while discharging the coolant through said coolant discharge passage.

2. A laser balloon catheter apparatus for emitting laser light received through an optical fiber via a balloon for irradiating tissue, comprising:
   laser light emitting means;
   a coolant supply passage located in said balloon for supplying a coolant thereto;
   a coolant discharge passage located in said balloon for discharging the coolant;
   coolant circulating means for supplying the coolant to the balloon through said coolant supply passage to inflate the balloon while discharging the coolant through said coolant discharge passage;
   temperature detecting means for detecting a temperature of the tissue which is irradiated with laser light; and
   means for adjusting the laser light emitting period of time per unit time in accordance with a signal representing the temperature of the tissue as detected by the temperature detecting means.

3. The laser balloon catheter apparatus according to claim 2, wherein:
   the temperature detecting means has a detecting end which is provided on a surface of the balloon.

4. A laser balloon catheter apparatus for emitting laser light received through an optical fiber via a balloon for irradiating tissue, comprising:
   a laser light emitting means;
   a first guide through which said optical fiber extends, having a front end portion located in the balloon and having at the front end portion a communicating hole which communicates an inside of the guide with an inside of the balloon;
   securing means for securing the front end portion of the optical fiber to the first guide;
   a second guide which is provided coaxially with and around the first guide, having a front end which communicates with the inside of the balloon; and
   coolant circulating means including a coolant supply passage which is one of a space in said first guide and a space between the first and second guides and a coolant discharge passage which is the other of the spaces, for supplying the coolant through said coolant supply passage to inflate the balloon while discharging the coolant through the coolant discharge passage; and
   a communicating hole for the coolant being formed through said securing means or between securing means and the first guide.

5. The laser balloon catheter apparatus according to claim 4, wherein:
   a mouth of the balloon is secured to the front end of the first guide.

6. The laser balloon catheter apparatus according to claim 4, wherein:
   said guide is made of a flexible material and has a balloon portion having a large diameter at the front end portion thereof, the balloon portion being sealingly secured at a front end thereof to a shoe member disposed in front of said laser light emitting means.

7. The laser balloon apparatus according to claim 1, wherein:
   an inside surface at a forward end of the coolant supply passage is roughened for scattering the laser light emitted from the end face of the optical fiber.

8. The laser balloon apparatus according to claim 1, wherein:

a front surface of the holder means is provided with a reflecting surface to reflect laser light through the coolant supply passage.

9. The laser balloon apparatus according to claim 2, wherein:

an inside surface at a forward end of the coolant supply passage is roughened for scattering the laser light emitted from the end face of the optical fiber.

10. The laser balloon apparatus according to claim 2, wherein:

a front surface of the holder means is provided with a reflecting surface to reflect laser light through the coolant supply passage.

* * * * *